United States Patent [19]
Pollock et al.

[11] Patent Number: 5,599,491
[45] Date of Patent: Feb. 4, 1997

[54] METHOD AND APPARATUS FOR MAKING A MOLD FOR DUPLICATING A POSITIVE MASTER

[75] Inventors: Benedikt Pollock, Essen; Albert Schröder, Wuppertal, both of Germany

[73] Assignee: Krupp Medizintechnik GmbH, Essen, Germany

[21] Appl. No.: 302,622

[22] Filed: Sep. 8, 1994

[30] Foreign Application Priority Data

Sep. 14, 1993 [DE] Germany ............ 43 31 148.2

[51] Int. Cl.⁶ ............ B29C 33/40; B29C 39/22
[52] U.S. Cl. ............ 264/138; 249/52; 249/54; 249/109; 249/112; 249/164; 249/167; 249/170; 264/225; 264/227; 425/175; 425/179
[58] Field of Search ............ 425/175, 179; 249/164, 167, 170, 54, 52, 112, 105, 109; 264/16, 225, 227, 138

[56] References Cited

U.S. PATENT DOCUMENTS

| | | | |
|---|---|---|---|
| 2,397,168 | 3/1946 | Touceda | 425/179 |
| 3,871,803 | 3/1975 | Beattie | 425/175 |
| 4,022,419 | 5/1977 | Haker | 249/54 |
| 4,119,292 | 10/1978 | Haker | 249/54 |
| 4,962,909 | 10/1990 | Kohler | 249/54 |
| 5,281,122 | 1/1994 | Langner | 249/54 |

FOREIGN PATENT DOCUMENTS

| | | | |
|---|---|---|---|
| 364837 | 12/1922 | Germany | 249/164 |
| 901581 | 1/1954 | Germany | 264/16 |
| 7800950 | 5/1978 | Germany . | |
| 3541719 | 5/1986 | Germany . | |

*Primary Examiner*—Robert Davis
*Attorney, Agent, or Firm*—Herbert Dubno; Andrew Wilford

[57] ABSTRACT

An apparatus for making a mold for forming positive models identical to a positive master has upper and lower mold shells having confronting and contiguous rims lying in respective planes. The shells are dimensioned when juxtaposed to spacedly contain the master. A clamp is engageable with the shells generally at the rims to hold the shells together with the plane of their rims spaced apart.

20 Claims, 7 Drawing Sheets

METHOD AND APPARATUS FOR MAKING A MOLD FOR DUPLICATING A POSITIVE MASTER

FIELD OF THE INVENTION

The present invention relates to making a mold. More particularly this invention concerns making a mold by means of a master for subsequent casting of models of the master.

BACKGROUND OF THE INVENTION

It is standard, for example, in the dental field to have to make a very accurate model of a patient's bite, for instance for the production of prosthetics, bridges, and the like. Thus a mold spoon filled with impression material is used to create a negative from which a positive of plaster or hard impression material is then made. In turn this positive is fitted in a mold that is filled around the positive with silicone or a similar elastic material that is then allowed to cure. Once cured, the positive master is separated from the material which therefore forms an accurate negative mold.

In the simplest procedure as described in German patent 3,541,719 filed 26 Nov. 1985 by H. Diehl the positive is provided with an imbedded magnet or magnetically attractable body and is held thereby to the floor of a mold-making mold. This mold floor is subsequently used as part of the final mold for forming the model.

German Utility Model 7,800,950 of A. Schmidseder describes a system where special supports are provided to hold the master between a pair of mold halves. After curing of an impression mass in the mold halves about the master, the mass can be separated at the level of the supports to split it into two halves and free the master. German patent application P 24 40 261.7 of G. Haker describes a retainer ring for holding together two mold halves of the type described in the Schmidseder system.

These systems do not make it simple or in some cases even possible to reproduce holding formations or so-called splits that are provided on the bottom of the master to hold it in an articulator or like holder. These formations, which can be specially formed bumps or recesses that engage with complementary formations of the articulator, are essential to subsequent working on the models.

OBJECTS OF THE INVENTION

It is therefore an object of the present invention to provide an improved apparatus for making a mold.

Another object is to provide such an improved apparatus which allows accurate reproduction of holding formations on models.

A further object is to provide an improved method that uses the apparatus to produce a model from a master.

SUMMARY OF THE INVENTION

An apparatus for making a mold for forming positive models identical to a positive master according to the invention has upper and lower mold shells having confronting and contiguous rims lying in respective planes, the shells being dimensioned when juxtaposed to spacedly contain the master. According to the invention a clamp is engageable with the shells generally at the rims to hold the shells together with the plane of their rims spaced apart.

Thus according to the invention the master is first fit to the lower mold shell and then the upper mold shell is set over the lower mold shell so that the mold shells spacedly surround and contain the master and the mold shells are secured together so that a lower rim of the upper shell is parallel to and spaced by a gap above an upper rim of the lower shell. An interior of the mold shells around the master is then filled with a mass of fluent molding compound that is then allowed to cure. A cutter blade is then inserted into the gap between the mold shells to cut the cured mass all around the master to separate the cured mass into an upper part in the upper shell forming therewith an upper mold half and a lower part in the lower shell forming therewith a lower mold half. The two mold halves are then separated to leave the master in one of the halves and form a mold-cavity half in the other mold half. The master is then removed from the one half to form therein another mold-cavity half and a fill hole is formed from the exterior into one of the mold-cavity halves and the two mold halves are reunited. Finally the reunited mold-cavity halves are filled with a fluent mass of model material. This mass is then cured and the mold is stripped in the standard manner.

It is also possible according to the invention for the top half to be formed by an annular side-wall part and a piston-like upper wall. In this case the wall is pushed down in the side-wall part after the master is installed in the lower part, and in fact the master can be set in the lower part after it is secured to the upper part.

According to the invention the mold shells are fixed together by securing a retaining clamp around them at outwardly projecting lips formed on the shells at the rims. In addition the bottom shell can be formed with upwardly projecting bumps. In this case it is possible to fit into the bottom shell a liner through which the bumps project and then set the master on the bumps. The fill hole in this system can be formed by stripping the bottom shell from the liner and respective part of the mass. The master is retained in the lower shell by means of a magnet.

The clamp ring according to this invention has a pair of half-ring parts that are movable relative to each other and closable over the rims of the shells. In particular each ring part is formed with a pair of parallel and spaced grooves for receiving the respective lips and is formed between the grooves with a wide ridge that projects between the rims and spaces them apart. The fitting includes a hinge interconnecting the two parts and a latch for securing it in place on the lips.

Although the bottom shell is provided with upstanding bumps on which the master can sit the mold can be used to reproduce the holding formations, the so-called splits, that are used to secure the model to an articulator or other holder. These bumps are integrally injection-molded with the bottom shell. Furthermore the bottom shell is provided with a liner which itself has the lip of the bottom shell and which is formed with apertures through which the bumps project. This liner is provided with a magnet and the bottom shell is provided with headed anchor studs. In addition the bottom shell is formed with at least one throughgoing fill hole and is provided with a plug for blocking the hole.

The upper shell according to the invention can have an annular wall part formed with the respective lip and a liner wall movable piston-like in the annular wall part. The upper region of this annular wall part has parallel walls, but the lower region flares downward. The liner wall can therefore move in the upper region.

BRIEF DESCRIPTION OF THE DRAWING

The above and other objects, features, and advantages will become more readily apparent from the following description, reference being made to the accompanying drawing in which.

SPECIFIC DESCRIPTION

As seen in FIGS. 1 through 5, a mold-making mold according to the invention has a bottom half or shell 20 of rounded triangular shape and an upper half or shell 25 of similar outline. The bottom shell 20 is formed with two throughgoing circular-section holes 21 that can be blocked by plugs 22. Its floor is provided with an array of star-headed anchor studs 23 and with a central permanent-magnet disk 37.

Figure 1:
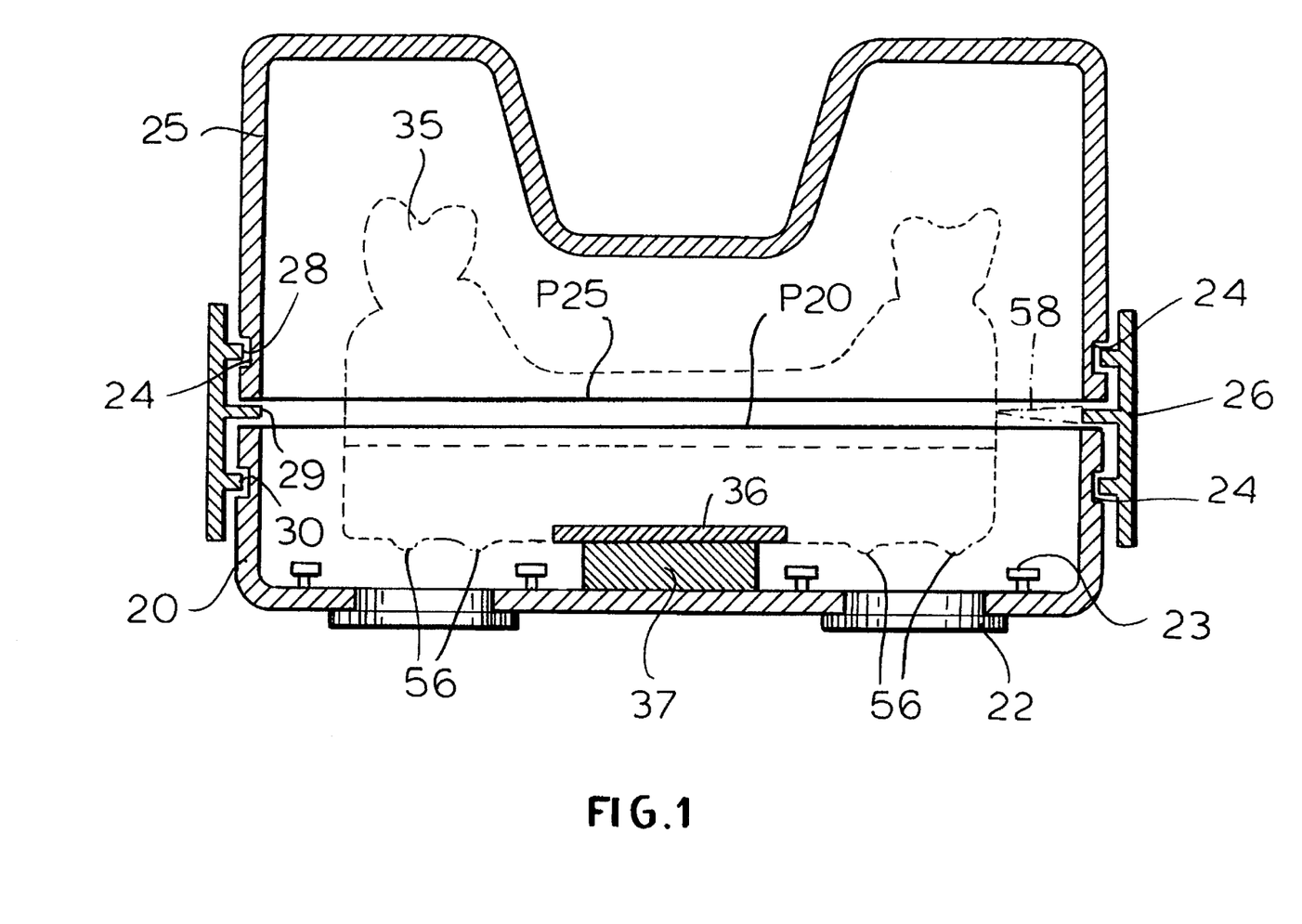
FIG. 1 is a vertical section through the mold-making apparatus of this invention.
Figure 2:
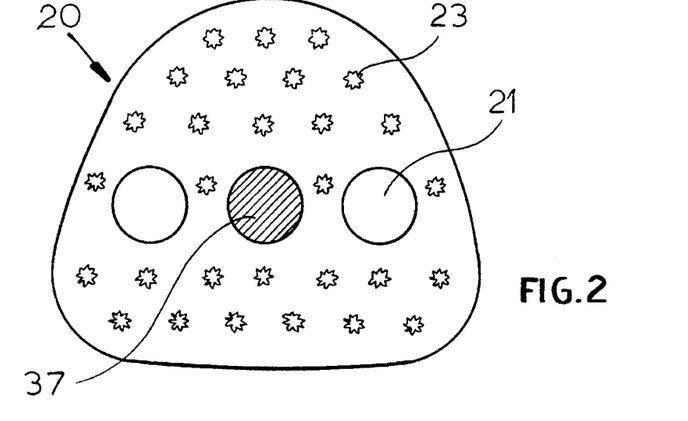
FIG. 2 is a top view of the bottom shell of the apparatus of FIG. 1.

The confronting rims of the upwardly open bottom shell 20 and downwardly open top shell 25 lie in respective planes P20 and P25 and each of the halves 20 and 25 is formed adjacent its rim with a respective outwardly open peripheral groove 24. When in use the halves 20 and 25 are secured together with the planes P20 and P25 parallel but spaced. A master 35 provided on its bottom with a magnetic or magnetically attractable plate 36 and with split formations 56 is held on the magnet 37 of the lower shell 20. The holes 21 are aligned with the splits 56.

Figure 3:
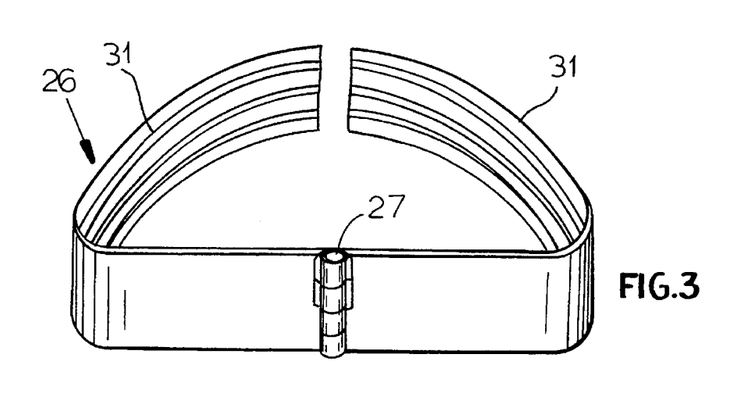
FIG. 3 is a perspective view of the retaining device for the mold-making apparatus.
Figure 4:
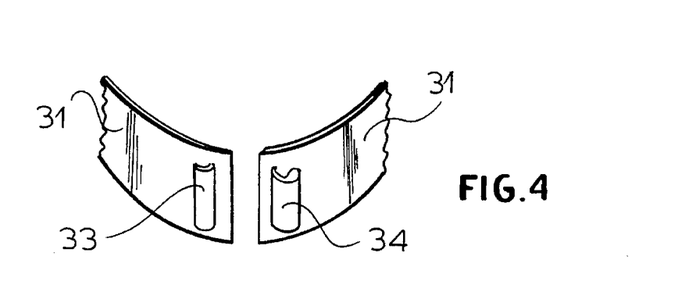
FIG. 4 is a perspective view of a detail of the retaining device.
Figure 5:
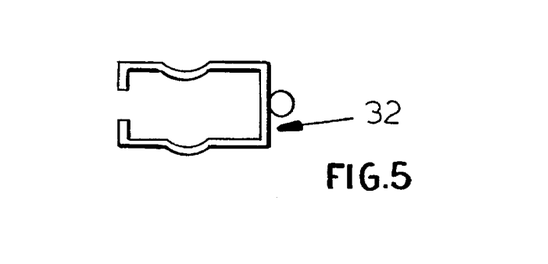
FIG. 5 is a top view of a clip usable on the retaining device.
Figure 6:
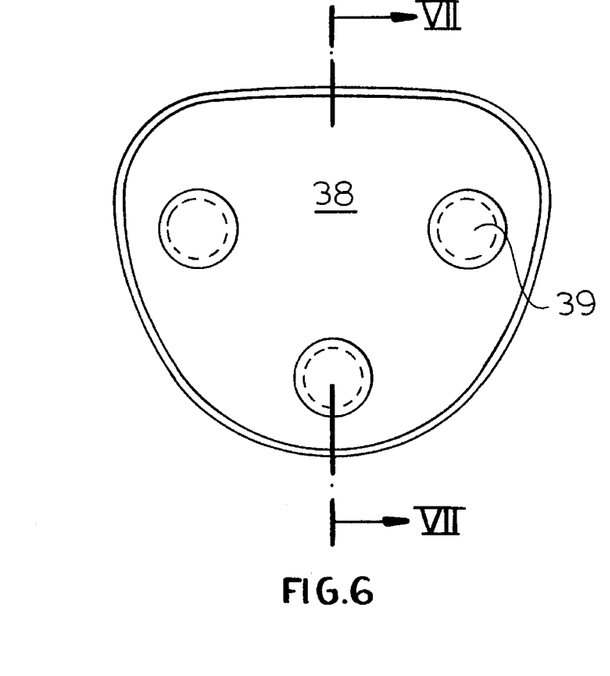
FIG. 6 is a top view of the bottom shell of another mold-making apparatus according to the invention.
Figure 7:
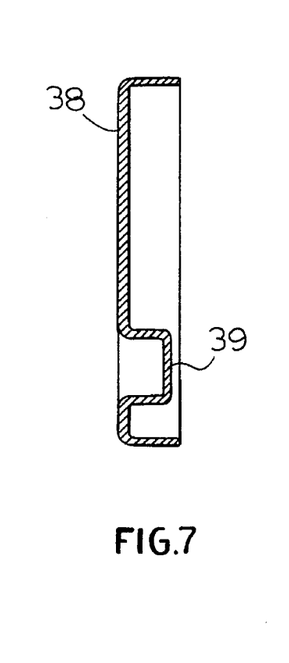
FIG. 7 is a section taken along line VII—VII of FIG. 6.
Figure 8:
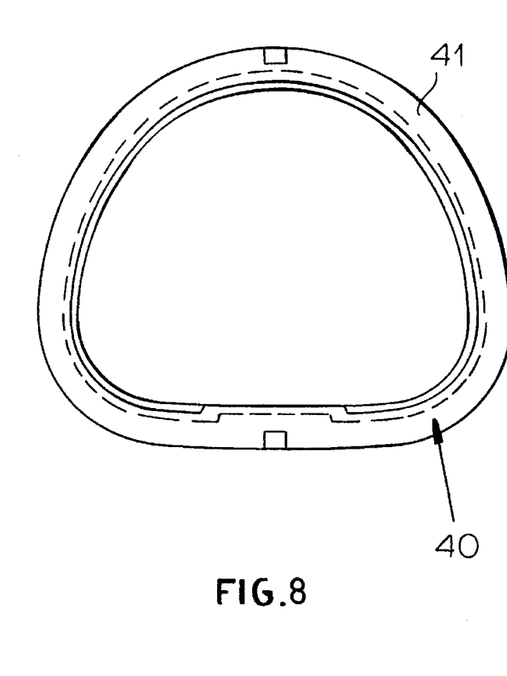
FIG. 8 is a bottom view of the top shell of the other mold-making apparatus according to the invention.
Figure 9:
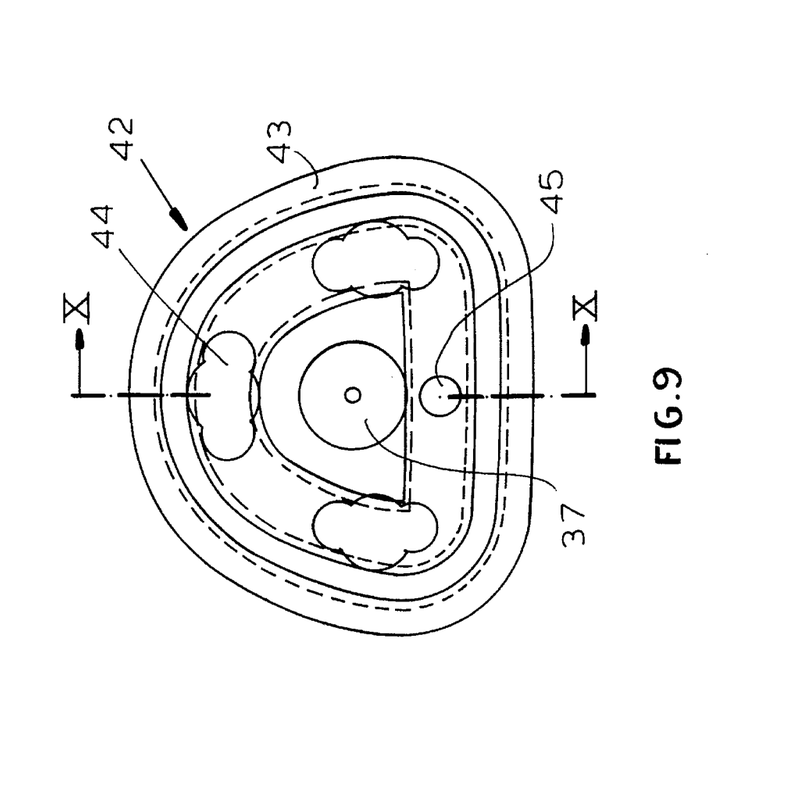
FIG. 9 is a top view of a liner for the bottom mold shell of FIGS. 6 and 7.
Figure 10:
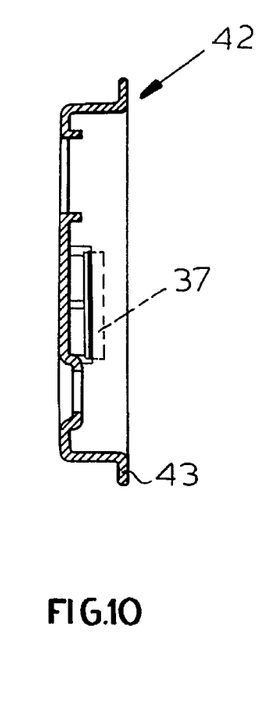
FIG. 10 is a section taken along line X—X of FIG. 9.
Figure 11:
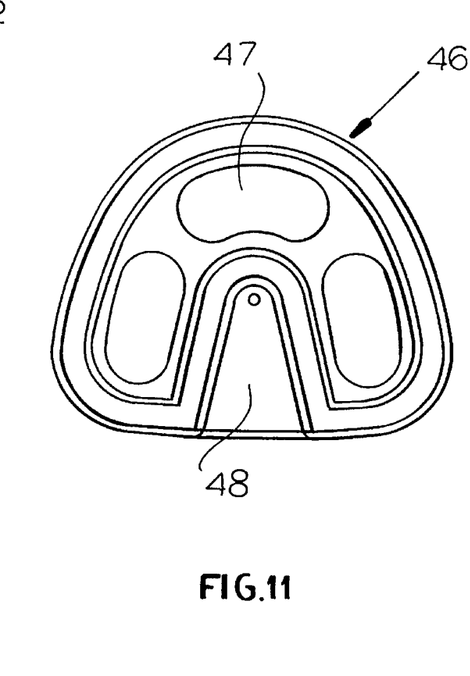
FIG. 11 is a top view of a cover plate or liner for the top shell of FIG. 8.

FIGS. 3 through 5 show a retaining device 26 formed as a pair of like generally C-shaped parts 31 hinged together at 27 and spaced apart at their opposite ends. The free ends of the parts 31 are provided with hooks 33 and 34 over which a retaining clip 32 can be snapped. The inner faces of the device 26 are formed with a pair of inwardly projecting ridges 28 adapted to fit in the grooves 24 and a wider central ridge 29 that fits between the halves 20 and 25 to hold the planes P20 and P25 apart.

As shown in FIGS. 14A through 14J this arrangement is used as follows:

First of all (FIG. 14A) the master 35 is positioned as described on the magnet 37 in the bottom shell 20. Then (FIG. 14B) the upper shell 25 is set in place and held at the described spacing by the retaining device 26 which is snapped around the two juxtaposed mold halves 20 and 25. Silicone is then (FIG. 14C) poured through an unillustrated opening in the top shell 25 to completely fill the mold 20, 25 around the master 35, completely imbedding the master 35 except where its magnetic plate 36 sits atop the magnet 37.

Figure 14A:
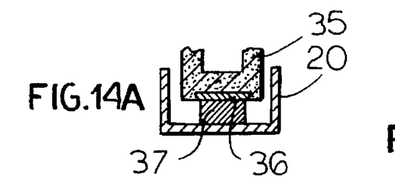
FIGS. 14A through 14J show the successive steps of using the apparatus of FIGS. 1 through 6.
Figure 14B:
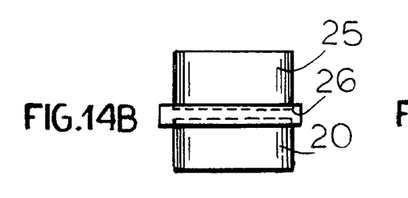
Figure 14C:
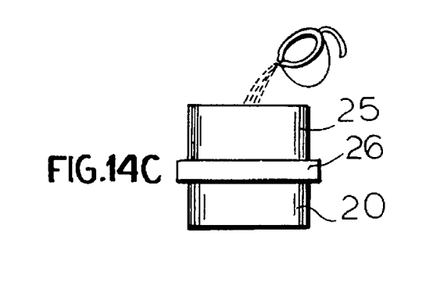
Figure 14D:
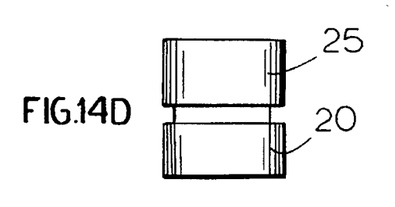
Figure 14E:
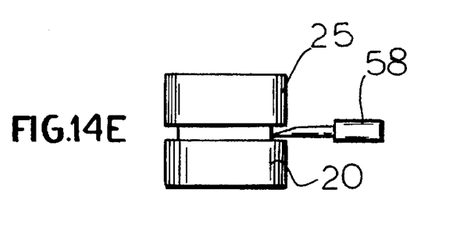
Figure 14F:
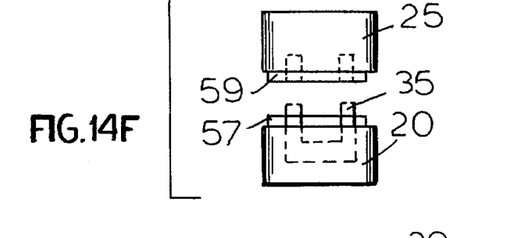
Figure 14G:
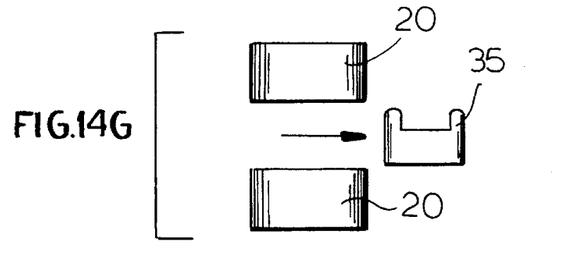

Once the molding compound is cured the device 26 is removed (FIG. 14D). A blade 58 (FIG. 1 also) is then (FIG. 14E) fitted between the halves 20 and 25 and is poked in to the master 35, then run peripherally completely around the master. This cuts the cured molding compound into two complementary pieces 57 and 59 along a central plane with each piece solidly stuck in its respective mold shell 20 or 25.

The upper mold half 25, 59 is then (FIG. 14F) pulled upward away from the lower half 20, 57, normally leaving the master 35 held in the lower shell 20. This master 35 is then (FIG. 14G) stripped from the lower half 20, 57.

Figure 14H:
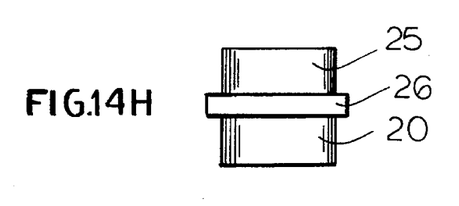
Figure 14I:
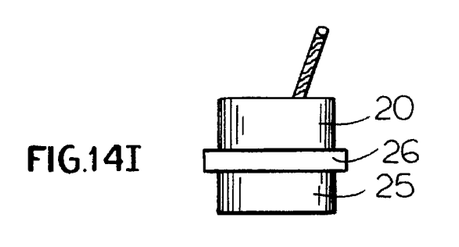
Figure 14J:
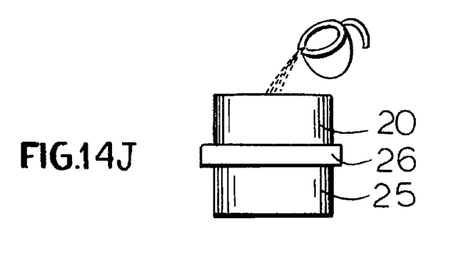

The two mold halves 20, 57 and 25, 59 thus created are reunited with the retaining device 26 (FIG. 14H). At least one of the plugs 22 is removed and the silicone mass is drilled or punched out through to the mold cavity at a location offset from the splits 56 (FIG. 14I) to make a fill hole. The material from which the model is to be made is then (FIG. 14J) poured in through this hole to create a model that is an accurate duplicate of the master 35, but of a different material. Once this material is cured the mold halves are separated as is known per se.

FIGS. 6 through 13 show an alternative system. Here a bottom mold shell 38 (FIGS. 6 and 7) is formed with three cylindrical bumps 39. A top shell 40 (FIG. 8) is annular and has at its bottom edge a perpendicularly outwardly projecting annular lip 41. This top shell 40 is slightly downwardly flared in its lower region but its side walls are parallel in an upper region. A liner 42 (FIGS. 9 and 10) for the bottom shell 38 is formed with three large openings 44 that engage at their sides on the bumps 39 while being spaced from them at their ends. It is also formed with a fourth fill opening 45 and is provided centrally with the magnet 37. Another liner 46 (FIG. 11) forms a top wall of the top shell 40 and is shaped so that it can slide down therein like a piston. It is formed with large openings 47 and with a nose-shaped depression 48.

Figures 12, 12A:
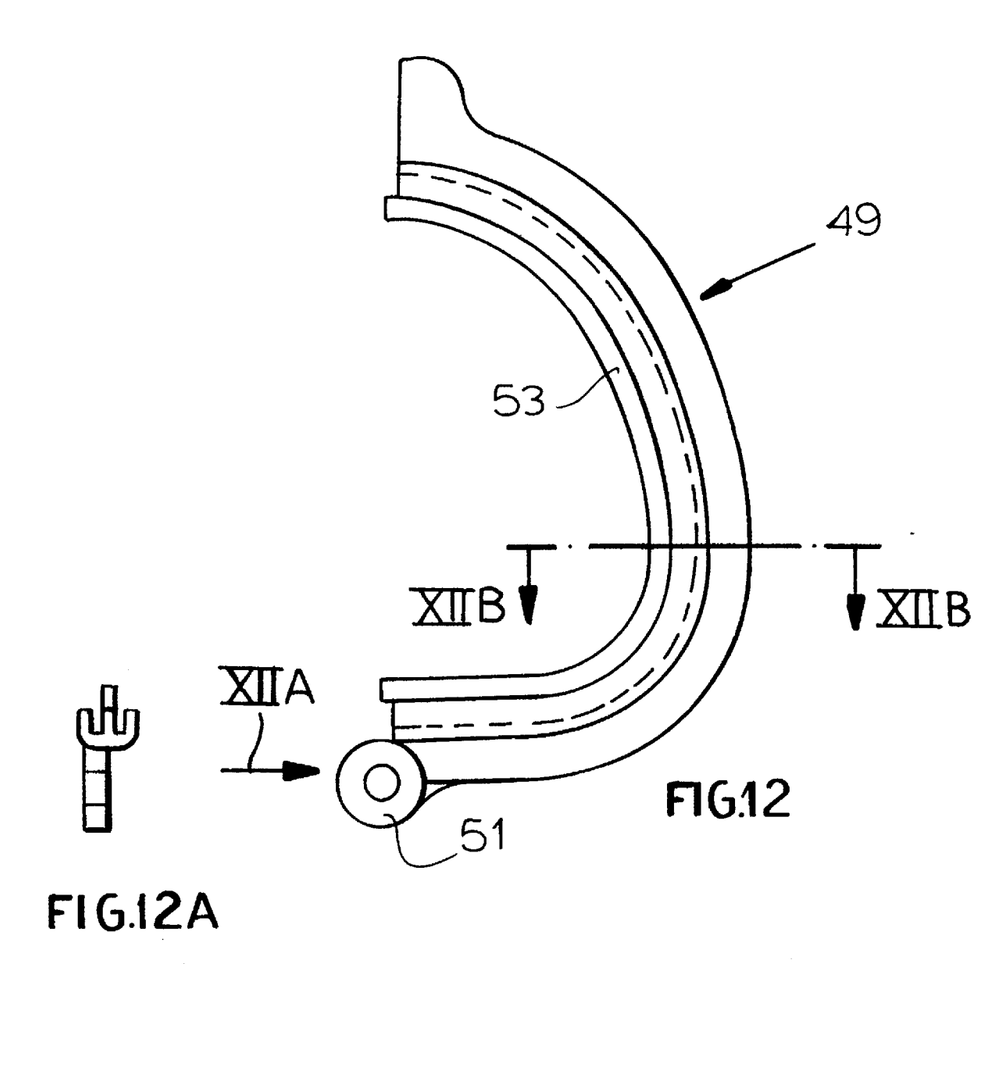
FIG. 12 is a top view of half of a retaining ring for the system of FIGS. 6 through 11.
FIG. 12A is a view taken in the direction of arrow XIIA of FIG. 12.
Figure 12B:
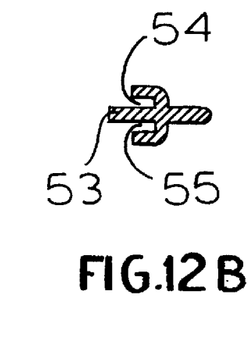
FIG. 12B is a cross section taken along line XIIB—XIIB of FIG. 12.
Figure 13:
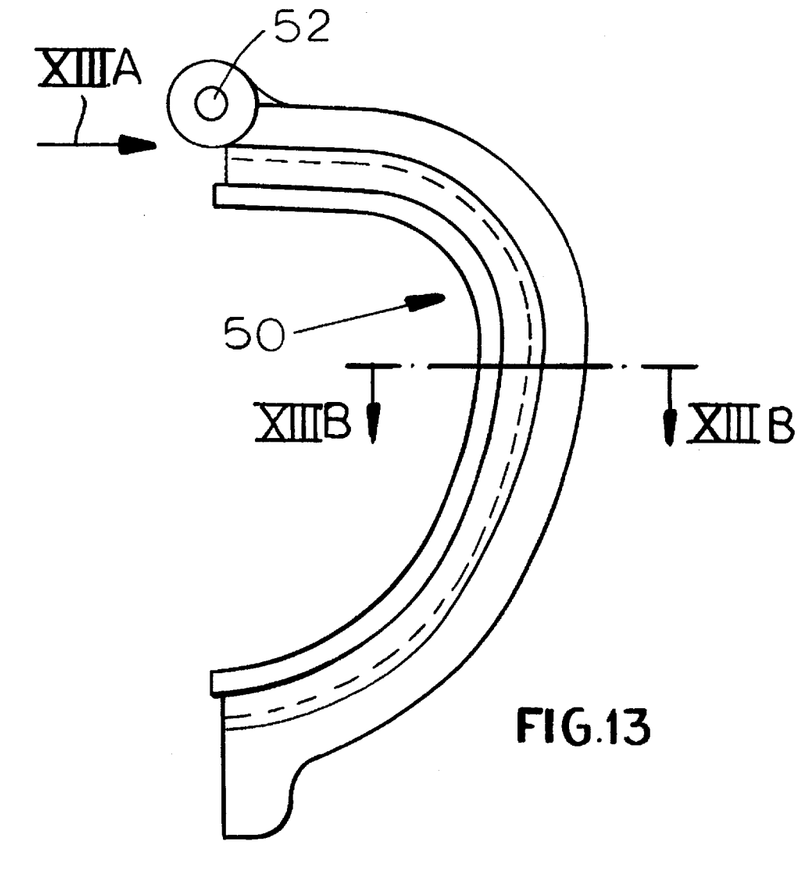
FIG. 13 is a top view of the other half of a retaining ring for the system of FIGS. 6 through 11.
Figure 13A:
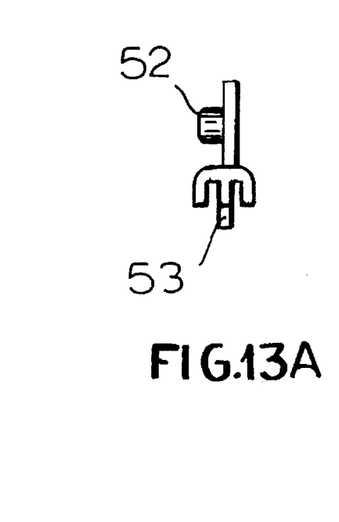
FIG. 13A is a view taken in the direction of arrow XIIIA of FIG. 13.
Figure 13B:
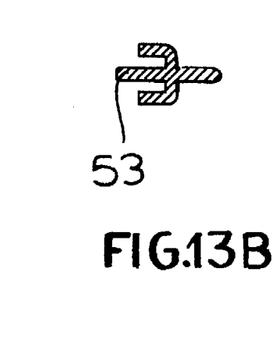
FIG. 13B is a cross section taken along line XIIIB—XIIIB of FIG. 13.

The retaining strap or device here has a pair of halves 49 and 50 that can be hinged together by an eye 5 formed on the part 49 and a pin 52 on the part 50. These parts 49 and 50 are shaped to fit around the rims 41 and 43 and have a pair of grooves 54 and 55 adapted to receive these rims 41 and 43, respectively and a central rib or lip 53 that functions like the lip 29 of FIG. 1 to form the desired space between the mold shells.

This device is used like that of FIGS. 1 through 6 except that the liner 37 is fitted to the bottom shell 38 and the top shell 40 without the liner 46 is fitted by the retaining device 49, 50 before the master 35 is installed in it to rest on the bumps 39 and magnet 37. Then the top liner 46 is pushed down in the parallel-wall section of the top half 40 until it is just above the master 35, and casting proceeds as described above. The liner 42 remains imbedded wholly in the bottom mold half formed in this manner. The plate 38 is stripped off to leave fill holes at the locations where the bumps 39 engaged the bottom of the master, although it might be necessary to punch through a thin web of the silicone in these locations.

We claim:

1. An apparatus for making a mold for forming positive models identical to a positive master, the apparatus comprising:

upper and lower mold shells having confronting and contiguous rims lying in respective planes, the shells being dimensioned when juxtaposed to spacedly contain the master and each being provided on its rim with an outwardly projecting lip; and retaining means including a pair of half-ring parts movable relative to each other and closable over the rims of the shells to hold the shells together with the planes of their rims spaced apart, each ring part being formed with a pair of parallel and spaced grooves for receiving the respective lips and being formed between the grooves with a wide ridge that projects between the rims and spaces them apart.

2. An apparatus for making a mold for forming positive models identical to a positive master, the apparatus comprising:

upper and lower mold shells having confronting and contiguous rims lying in respective planes, the shells being dimensioned when juxtaposed to spacedly contain the master, the lower shell being provided with upstanding bumps on which the master can sit; and retaining means engageable with the shells generally at the rims to hold the shells together with the planes of their rims spaced apart.

3. The mold-making apparatus defined in claim 2 wherein each shell is provided on its rim with an outwardly projecting lip.

4. The mold-making apparatus defined in claim 3 wherein the retaining means includes an annular fitting engageable around the shells on the rims thereof.

5. The mold-making apparatus defined in claim 4 wherein the fitting has a pair of half-ring parts that are movable relative to each other and closable over the rims of the shells.

6. The mold-making apparatus defined in claim 5 wherein each ring part is formed with a pair of parallel and spaced grooves for receiving the respective lips and is formed between the grooves with a wide ridge that projects between the rims and spaces them apart.

7. The mold-making apparatus defined in claim 5 wherein the fitting includes a hinge interconnecting the two parts.

8. The mold-making apparatus defined in claim 7 wherein the fitting is provided with a latch for securing it in place on the lips.

9. The mold-making apparatus defined in claim 2 wherein the bumps are integrally injection-molded with the lower shell.

10. The mold-making apparatus defined in claim 2 wherein the lower shell is provided with a liner which itself has the lip of the lower shell and which is formed with apertures through which the bumps project.

11. The mold-making apparatus defined in claim 10 wherein the liner is provided with a magnet.

12. An apparatus for making a mold for forming positive models identical to a positive master, the apparatus comprising:

upper and lower mold shells having confronting and contiguous rims lying in respective planes, the shells being dimensioned when juxtaposed to spacedly contain the master, the lower shell being provided with headed anchor studs; and retaining means engageable with the shells generally at the rims to hold the shells together with the planes of their rims spaced apart.

13. An apparatus for making a mold for forming positive models identical to a positive master, the apparatus comprising:

upper and lower mold shells having confronting and contiguous rims lying in respective planes, the shells being dimensioned when juxtaposed to spacedly contain the master, the lower shell being formed with at least one throughgoing fill hole and being provided with a plug for blocking the hole; and retaining means engageable with the shells generally at the rims to hold the shells together with the planes of their rims spaced apart.

14. An apparatus for making a mold for forming positive models identical to a positive master, the apparatus comprising:

upper and lower mold shells having confronting and contiguous rims lying in respective planes, the shells being dimensioned when juxtaposed to spacedly contain the master, the upper shell having an annular wall part formed with the respective lip and a liner wall movable in the annular wall part; and retaining means engageable with the shells generally at the rims to hold the shells together with the planes of their rims spaced apart.

15. The mold-making apparatus defined in claim 1 wherein the shells are made of a hard plastic.

16. A method of making a mold for casting positive models identical to a positive master, the method comprising the steps of sequentially:

a) fitting the master in a lower mold shell;

b) setting an upper mold shell over the lower mold shell so that the mold shells spacedly surround and contain the master;

c) securing the mold shells together so that a lower rim of the upper shell is parallel to and spaced by a gap above an upper rim of the lower shell;

d) filling an interior of the mold shells around the master with a mass of fluent molding compound;

e) curing the mass of compound to a solid;

f) inserting a cutter blade into the gap between the mold shells and cutting the cured mass all around the master to separate the cured mass into an upper part in the upper shell forming therewith an upper mold half and a lower part in the lower shell forming therewith a lower mold half;

g) separating the two mold halves and leaving the master in one of the halves and forming a mold-cavity half in the other half;

h) removing the master from the one half to form therein another mold-cavity half;

i) forming a fill hole from outside into one of the mold-cavity halves and reuniting the two mold halves; and j) filling the reunited mold-cavity halves with a fluent mass of model material.

17. The method defined in claim 16 wherein the mold shells are secured together by securing a retaining clamp around them at outwardly projecting lips formed on the shells at the rims.

18. The method defined in claim 16 wherein the lower shell is formed with upwardly projecting bumps, further comprising the step before step a) of fitting into the lower shell a liner through which the bumps project and then in step a) setting the master on the bumps, the fill hole being formed by stripping the lower shell from the liner and respective part of the mass.

19. The method defined in claim 16 wherein the upper half is formed by an annular side-wall part and a piston upper wall, the wall being pushed down in the sidewall part after the master is installed in the lower part.

20. The method defined in claim 16, further comprising the step of retaining the master in the lower shell by means of a magnet.

* * * * *